(12) United States Patent
Wen

(10) Patent No.: US 7,922,490 B2
(45) Date of Patent: Apr. 12, 2011

(54) BASE FOR PHYSICAL DENTAL ARCH MODEL

(75) Inventor: Huafeng Wen, Redwood City, CA (US)

(73) Assignee: Align Technology, Inc., San Jose, CA (US)

( * ) Notice: Subject to any disclaimer, the term of this patent is extended or adjusted under 35 U.S.C. 154(b) by 1394 days.

(21) Appl. No.: 11/013,152

(22) Filed: Dec. 14, 2004

(65) Prior Publication Data

US 2006/0127853 A1    Jun. 15, 2006

(51) Int. Cl.
*A61C 11/00* (2006.01)
*A61C 13/34* (2006.01)

(52) U.S. Cl. .............................. 433/213; 433/54; 433/74

(58) Field of Classification Search .................... 433/34, 433/24, 29, 213, 54, 74
See application file for complete search history.

(56) References Cited

U.S. PATENT DOCUMENTS

| | | | | |
|---|---|---|---|---|
| 1,813,583 A | * | 7/1931 | Rice | 433/213 |
| 2,037,344 A | * | 4/1936 | Schwartz | 425/178 |
| 2,138,254 A | * | 11/1938 | Mink | 433/56 |
| 2,700,218 A | * | 1/1955 | Lindley | 433/213 |
| 3,218,711 A | | 11/1965 | Connan | |
| 3,436,829 A | | 4/1969 | Jermyn | |
| 3,453,736 A | * | 7/1969 | Waltke | 433/74 |
| 3,470,614 A | * | 10/1969 | Kelly | 433/36 |
| 3,576,075 A | * | 4/1971 | Scott | 433/34 |
| 3,702,027 A | * | 11/1972 | Marshall et al. | 433/34 |
| 3,760,503 A | * | 9/1973 | Baskas | 433/90 |
| 3,890,710 A | | 6/1975 | Jaeger | |
| 3,905,106 A | * | 9/1975 | Costa et al. | 433/213 |
| 3,932,939 A | * | 1/1976 | Weissman | 433/213 |
| 3,937,773 A | * | 2/1976 | Huffman | 264/17 |
| 4,122,606 A | * | 10/1978 | Roman | 433/213 |
| 4,173,505 A | | 11/1979 | Jacobs | |
| 4,203,219 A | | 5/1980 | Wiener | |
| 4,265,619 A | | 5/1981 | Lucki et al. | |
| 4,368,042 A | | 1/1983 | Felstead et al. | |
| 4,374,076 A | | 2/1983 | Stephan et al. | |
| 4,475,888 A | | 10/1984 | Gores et al. | |
| 4,494,934 A | * | 1/1985 | Huffman | 433/213 |
| 4,529,384 A | | 7/1985 | Severy | |
| 4,657,992 A | | 4/1987 | Brennan et al. | |
| 4,755,139 A | | 7/1988 | Abbatte et al. | |
| 4,767,330 A | * | 8/1988 | Burger | 433/213 |
| 4,798,534 A | | 1/1989 | Breads | |
| 4,828,117 A | * | 5/1989 | Panzera et al. | 206/63.5 |
| 4,834,651 A | | 5/1989 | Fenick | |
| 4,856,991 A | | 8/1989 | Breads et al. | |
| 4,936,862 A | | 6/1990 | Walker et al. | |
| 4,943,237 A | | 7/1990 | Bryan | |
| 5,011,405 A | | 4/1991 | Lemchen | |
| 5,035,613 A | | 7/1991 | Breads et al. | |
| 5,055,039 A | | 10/1991 | Abbatte et al. | |
| 5,059,118 A | | 10/1991 | Breads et al. | |
| 5,131,844 A | | 7/1992 | Maranccio et al. | |
| 5,186,623 A | | 2/1993 | Breads et al. | |
| 5,273,429 A | | 12/1993 | Rekow et al. | |
| 5,338,198 A | | 8/1994 | Wu et al. | |
| 5,340,309 A | | 8/1994 | Robertson | |

(Continued)

*Primary Examiner* — Cris L Rodriguez
*Assistant Examiner* — Michael R Ballinger

(57) ABSTRACT

A method produces a base for physical tooth models. The method includes providing one or more cast materials in a container, pressing the underside of the physical tooth models into the one or more cast materials to produce impressions in the one or more cast materials, and solidifying the one or more cast materials having the impressions to produce the base that is adapted to receive the physical tooth models.

32 Claims, 13 Drawing Sheets

U.S. PATENT DOCUMENTS

| | | | |
|---|---|---|---|
| 5,342,202 A | 8/1994 | Deshayes | |
| 5,368,478 A | 11/1994 | Andreiko et al. | |
| 5,382,164 A | 1/1995 | Stern | |
| 5,452,219 A | 9/1995 | Dehoff et al. | |
| 5,466,152 A * | 11/1995 | Walter | 433/60 |
| RE35,263 E * | 6/1996 | Silva et al. | 433/74 |
| 5,549,476 A | 8/1996 | Stern | |
| 5,587,912 A | 12/1996 | Andersson et al. | |
| 5,607,305 A | 3/1997 | Andersson et al. | |
| 5,616,899 A | 4/1997 | Recigno | |
| 5,645,421 A | 7/1997 | Slootsky | |
| 5,647,744 A | 7/1997 | Squicciarini | |
| 5,788,489 A | 8/1998 | Huffman | |
| 5,879,158 A | 3/1999 | Doyle et al. | |
| 5,911,580 A | 6/1999 | Sharp et al. | |
| 5,927,984 A * | 7/1999 | Lin | 433/218 |
| 5,975,893 A | 11/1999 | Chishti et al. | |
| 6,217,325 B1 | 4/2001 | Chishti et al. | |
| 6,217,326 B1 | 4/2001 | Hahn | |
| 6,227,850 B1 | 5/2001 | Chishti et al. | |
| 6,227,851 B1 | 5/2001 | Chishti et al. | |
| 6,261,098 B1 | 7/2001 | Persson | |
| 6,299,440 B1 | 10/2001 | Phan et al. | |
| 6,309,215 B1 | 10/2001 | Phan et al. | |
| 6,386,865 B1 | 5/2002 | Suh et al. | |
| 6,423,252 B1 | 7/2002 | Chun et al. | |
| 6,425,759 B1 * | 7/2002 | Cronin | 433/34 |
| 6,497,574 B1 | 12/2002 | Miller | |
| 6,499,997 B2 | 12/2002 | Chishti et al. | |
| 6,524,101 B1 | 2/2003 | Phan et al. | |
| 6,541,074 B2 | 4/2003 | Cho | |
| 6,554,611 B2 | 4/2003 | Chishti et al. | |
| 6,572,372 B1 | 6/2003 | Phan et al. | |
| 6,582,227 B2 | 6/2003 | Phan et al. | |
| 6,582,229 B1 | 6/2003 | Miller et al. | |
| 6,602,070 B2 | 8/2003 | Miller et al. | |
| 6,607,382 B1 | 8/2003 | Kuo et al. | |
| 6,621,491 B1 | 9/2003 | Baumrind et al. | |
| 6,626,666 B2 | 9/2003 | Chishti et al. | |
| 6,626,669 B2 | 9/2003 | Zegarelli | |
| 6,629,840 B2 | 10/2003 | Chishti et al. | |
| 6,633,789 B1 | 10/2003 | Nikolskiy et al. | |
| 6,665,570 B2 | 12/2003 | Pavloskaia et al. | |
| 6,682,346 B2 | 1/2004 | Chishti et al. | |
| 6,685,469 B2 | 2/2004 | Chishti et al. | |
| 6,685,470 B2 | 2/2004 | Chishti et al. | |
| 6,688,886 B2 | 2/2004 | Hughes et al. | |
| 6,699,037 B2 | 3/2004 | Chishti et al. | |
| 6,705,861 B2 | 3/2004 | Chishti et al. | |
| 6,722,880 B2 | 4/2004 | Chishti et al. | |
| 6,726,478 B1 | 4/2004 | Isiderio et al. | |
| 6,729,876 B2 | 5/2004 | Chishti et al. | |
| 6,846,179 B2 | 1/2005 | Chapouland et al. | |
| 6,882,894 B2 | 4/2005 | Durbin et al. | |
| 6,884,068 B2 | 4/2005 | Huffman | |
| 6,913,462 B2 * | 7/2005 | Honstein et al. | 433/57 |
| 6,923,649 B2 | 8/2005 | Oswald et al. | |
| 6,981,874 B2 | 1/2006 | Allred et al. | |
| 7,040,897 B2 | 5/2006 | Fischer | |
| 7,048,031 B2 | 5/2006 | Usui | |
| 7,153,135 B1 | 12/2006 | Thomas | |
| 7,186,760 B2 | 3/2007 | Rudo | |
| 7,250,611 B2 * | 7/2007 | Aguirre et al. | 250/461.1 |
| 2001/0002310 A1 | 5/2001 | Chishti et al. | |
| 2001/0027401 A1 | 10/2001 | Klein | |
| 2001/0037248 A1 | 11/2001 | Klein | |
| 2002/0015934 A1 | 2/2002 | Rubbert et al. | |
| 2002/0017998 A1 | 2/2002 | Price | |
| 2002/0150855 A1 | 10/2002 | Chishti et al. | |
| 2002/0187451 A1 | 12/2002 | Phan et al. | |
| 2003/0002089 A1 | 1/2003 | Vadnais et al. | |
| 2003/0003416 A1 | 1/2003 | Chishti et al. | |
| 2003/0039940 A1 | 2/2003 | Miller | |
| 2003/0203334 A1 | 10/2003 | Hedge et al. | |
| 2003/0207227 A1 | 11/2003 | Abolfathi | |
| 2004/0023185 A1 | 2/2004 | Gittleman | |
| 2004/0063060 A1 * | 4/2004 | Meyers et al. | 433/29 |
| 2004/0109783 A1 | 6/2004 | Prasad et al. | |
| 2004/0115587 A1 | 6/2004 | Breining et al. | |
| 2004/0197728 A1 | 10/2004 | Abolfathi et al. | |
| 2004/0234929 A1 | 11/2004 | Fischer et al. | |
| 2005/0003319 A1 | 1/2005 | Kuo | |
| 2005/0186150 A1 | 8/2005 | Allred | |
| 2005/0186526 A1 | 8/2005 | Stewart et al. | |
| 2006/0093982 A1 | 5/2006 | Wen | |
| 2006/0093987 A1 | 5/2006 | Wen | |
| 2006/0093992 A1 | 5/2006 | Wen | |
| 2006/0093993 A1 | 5/2006 | Wen | |
| 2006/0127838 A1 | 6/2006 | Liu et al. | |
| 2006/0127850 A1 | 6/2006 | Wen | |
| 2006/0127851 A1 | 6/2006 | Wen | |
| 2006/0134580 A1 | 6/2006 | Raby et al. | |
| 2006/0275736 A1 | 12/2006 | Wen et al. | |

* cited by examiner

BASE FOR PHYSICAL DENTAL ARCH MODEL

TECHNICAL FIELD

This application generally relates to the field of dental care, and more particularly to a system and a method for manufacturing and constructing a physical dental arch model.

CROSS-REFERENCES TO RELATED INVENTIONS

The present invention is related to concurrently filed and commonly assigned U.S. patent application Ser. No. 11/012,924, titled "Accurately producing a base for physical dental arch model" by Huafeng Wen, concurrently filed and commonly assigned U.S. patent application Ser. No. 11/013,145, titled "Fabricating a base compatible with physical dental tooth models" by Huafeng Wen, concurrently filed and commonly assigned U.S. patent application Ser. No. 11/013,156, titled "Producing non-interfering tooth models on a base" by Liu et al, concurrently filed and commonly assigned U.S. patent application Ser. No. 11/013,160, titled "System and methods for casting physical tooth model" by Liu et al, concurrently filed and commonly assigned U.S. patent application Ser. No. 11/013,159, titled "Producing a base for accurately receiving dental tooth models" by Huafeng Wen, and concurrently filed and commonly assigned U.S. patent application Ser. No. 11/013,157, titled "Producing accurate base for a dental arch model" by Huafeng Wen.

The present invention is also related to commonly assigned U.S. patent application Ser. No. 10/979,823, titled "Method and apparatus for manufacturing and constructing a physical dental arch model" by Huafeng Wen, Nov. 2, 2004, commonly assigned U.S. patent application Ser. No. 10/979,497, titled "Method and apparatus for manufacturing and constructing a dental aligner" by Huafeng Wen, Nov. 2, 2004, commonly assigned U.S. patent application Ser. No. 10/979,504, titled "Producing an adjustable physical dental arch model" by Huafeng Wen, Nov. 2, 2004, and commonly assigned U.S. patent application Ser. No. 10/979,824, titled "Producing a base for physical dental arch model" by Huafeng Wen, Nov. 2, 2004. The disclosure of these related applications are incorporated herein by reference.

BACKGROUND

Orthodontics is the practice of manipulating a patient's teeth to provide better function and appearance. In treatments using fixed appliance, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists and dentists typically review patient data such as X-rays and models such as impressions of teeth. They can then determine a desired orthodontic goal for the patient. With the goal in mind, the orthodontists place the brackets and/or bands on the teeth and manually bend (i.e., shape) wire, such that a force is asserted on the teeth to reposition the teeth into the desired positions. As the teeth move towards the desired position, the orthodontist makes continual adjustments based on the progress of the treatment.

U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,176 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth."

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target arch form and appliance design. Hence the '562 patent teaches away from an interactive, computer-based system in which the orthodontist remains fully involved in patient diagnosis, appliance design, and treatment planning and monitoring.

More recently, removable appliances from companies such as Align Technology, Inc. began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

SUMMARY

The present invention has been devised to provide a practical, effective and efficient methods and apparatus to manufacture and construct the physical dental arch model.

In one aspect, the present invention relates to a method for producing a base for physical tooth models, including providing cast materials in a container; pressing the underside of the physical tooth models into the cast materials to produce impressions in the cast materials; and solidifying the cast materials having the impressions to produce the base that is adapted to receive the physical tooth models.

In another aspect, the present invention relates to a method for producing a base for physical tooth models, including placing the physical tooth models in a container; pouring the cast materials over the underside of the physical tooth models in the container; and solidifying the cast materials having the impressions to produce the base that is adapted to receive the physical tooth models.

In yet another aspect, the present invention relates to a method for producing a base for a dental arch model, comprising:

transferring a cast materials in a container;

placing the underside of a physical tooth model in the container such that the underside of the physical tooth model produces an impression in the cast materials;

solidifying the cast materials having the impressions to produce a base component; and assembling a plurality of base components to form the base configured to receive the dental arch model.

Implementations of the system may include one or more of the following. A method for producing a base for physical tooth models includes providing cast materials in a container, pressing the underside of the physical tooth models into the cast materials to produce impressions in the cast materials, and solidifying the cast materials having the impressions to produce the base that is adapted to receive the physical tooth models. The casting a material can be selected from the group consisting of polymers, thermal elastic materials, urethane, epoxy, plaster, clay, acrylic, latex, dental PVS, resin, metal, aluminum, ice, wax, sand, and stone. The method can further include labeling the physical tooth models in a predetermined sequence that define the positions of the physical tooth models on the base. The method can further include defining the positions of the impressions on the base such that the physical tooth models received by the impressions form at least a portion of an arch. The method can further include defining the positions of the impressions on the base in accordance with a digital arch models. The digital arch model can be produced by scanning and digitizing a patient arch. The method can further include cooling the cast materials to cause the solidification of the cast materials having the impressions. The method can further include illuminating UV irradiation on the cast materials to cause the solidification of the cast materials having the impressions. The method can further comprise applying crosslinking agents to the cast materials to cause the polymerization and solidification of the cast materials having the impressions. The physical tooth models can include first features to assist the reception of the physical tooth models by the base. The features can comprise one or more of a pin, a registration slot, a notch, a protrusion, a hole, an interlocking mechanism, a jig, and a pluggable or attachable feature. The impressions in the base can comprise second features complimentary to the first features to assist the reception of the physical tooth models by the base. The tooth models can comprise a material selected from the group consisting of polymers, urethane, epoxy, plastics, plaster, stone, clay, acrylic, metals, wood, paper, ceramics, and porcelain.

Implementations of the system may include one or more of the following. A method for producing a base for physical tooth models includes placing the physical tooth models in a container, pouring the cast materials over the underside of the physical tooth models in the container, and solidifying the cast materials having the impressions to produce the base that is adapted to receive the physical tooth models. The casting a material can be selected from the group consisting of polymers, thermal elastic materials, urethane, epoxy, plaster, clay, acrylic, latex, dental PVS, resin, metal, aluminum, ice, and wax. The physical tooth models can comprise first features to assist the reception of the physical tooth models by the base.

Implementations of the system may include one or more of the following. The base components can comprise features to assist the assembly of the base components to form the base for the dental arch model. The features comprise one or more of a pin, a registration slot, a socket, a notch, a protrusion, a hole, an interlocking mechanism, a jig, and a pluggable or attachable feature.

Embodiments may include one or more of the following advantages. An advantage of the present invention is that a base for receiving dental tooth models can be produced with simple, inexpensive and reliable methods and system. The casting chambers are can be used multiple times to reduce manufacturing cost. Furthermore, the base can be molded in a plurality of components. Only a component of the base needs to be re-molded if the position of one physical tooth model is changed in an orthodontic treatment. This further reduces treatment cost.

The physical tooth models include features to allow them to be attached, plugged or locked to a base. The physical tooth models can be pre-fabricated having standard registration and attaching features for assembling. The physical tooth models can be automatically assembled onto a base by a robotic arm under computer control. The manufacturable components can be attached to a base. The assembled physical dental arch model specifically corresponds to the patient's arch. There is no need for complex and costly mechanisms such as micro-actuators for adjusting multiple degrees of freedom for each tooth model. The described methods and system is simple to make and easy to use.

Yet another advantageous feature of the disclosed system and methods is that the physical tooth models in the physical dental arch model can be easily separated, repaired or replaced, and reassembled after the assembly without the replacement of the whole arch model.

The physical dental arch model obtained by the disclosed system and methods can be used for various dental applications such as dental crown, dental bridge, aligner fabrication, biometrics, and teeth whitening. The arch model can be assembled from segmented manufacturable components that can be individually manufactured by automated, precise numerical manufacturing techniques.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention.

DESCRIPTION

Figure 1:
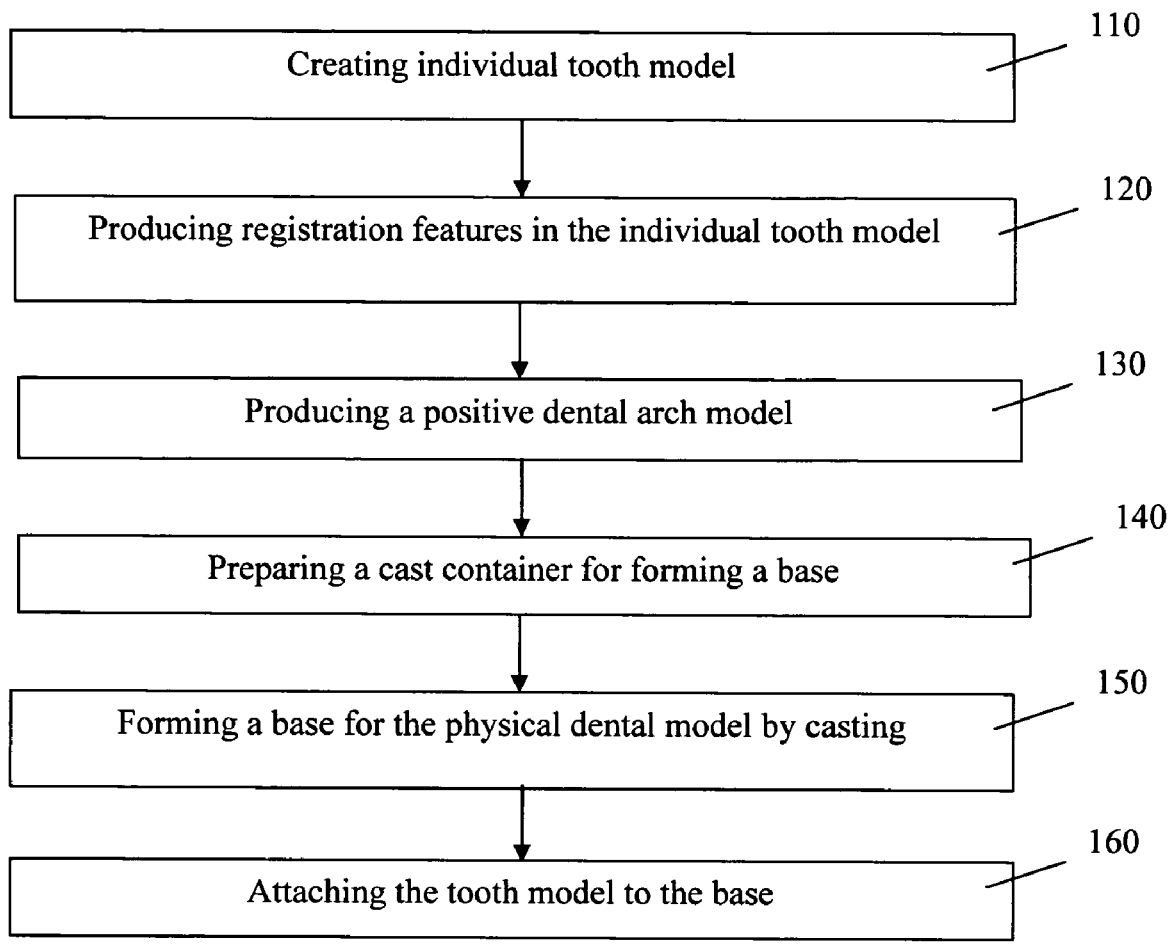
FIG. 1 is a flow chart for producing a physical dental arch model.

FIG. 1 shows an exemplary process for producing a physical dental arch model First individual tooth model is created in step 110. An individual tooth model can be a physical model that can be part of a physical tooth arch model, which can be used in various dental applications. Registration features are next added to the individual tooth model to allow them to be attached to each other or a base in step 120. A positive dental arch is produced in step 130. A cast container is prepared by forming a base in step 140. A base is fabricated by casting in step 150. The base includes features for receiving the individual tooth model. The tooth models are finally attached to the base at the predetermined positions using the pre-designed features in step 160.

Details of process in FIG. 1 are now described. Individual tooth model can be obtained in step 110 using a number of different methods. In one embodiment, the tooth model can be created by casting. A negative impression is first made from a patient's arch using for example PVS. A mold or a positive of the patient's arch is next made by pouring a casting material into the negative impression and allowing the mold to dry to obtain a positive model of the arch with teeth mounted thereon. In an alternative approach, a negative impression of the patient's arch is placed in a specially designed container. The undersides of the tooth models are placed upward. A casting material is then poured onto the underside of the container over the impression to create a model. A lid is subsequently placed over the container. The container is opened and the mold can be removed after the specified time. Examples of casting materials include auto polymerizing acrylic resin, thermoplastic resin, light-polymerized acrylic resins, polymerizing silicone, polyether, plaster, epoxies, or a mixture of materials. The casting material for molding the tooth models can be selected based on the uses of the cast. The material should be easy for cutting to obtain individual tooth model. Additionally, the material needs to be strong enough for the tooth model to take the pressure in pressure form for producing a dental aligner. Details of making a dental aligner are disclosed in commonly assigned and above referenced US patent application titled "Method and apparatus for manufacturing and constructing a dental aligner" by Huafeng Wen, filed Nov. 2, 2004, the content of which is incorporated herein by reference.

Features that allow tooth models to be attached to a base (step 120) can be added to the casting material in the casting process. Registration points or pins can be added to each tooth before the casting material has dried. Optionally, universal joints can be inserted at the top of the casting chamber using specially designed lids, which would hang the universal joints directly into the casting area for each tooth.

Still in step 110, individual tooth models are next cut from the arch positive. One requirement for cutting is to obtain individual teeth in such a manner that they can be joined again to form a tooth arch. The separation of individual teeth from the mold can be achieved using a number of different cutting methods including laser cutting and mechanical sawing.

Separating the positive mold of the arch into tooth models may result in the loss of the relative 3D coordinates of the individual tooth models in an arch. Several methods are provided in step 120 for finding relative position of the tooth models. In one embodiment, unique registration features are added to each pair of tooth models before the positive arch mold is separated. The separated tooth models can be assembled to form a physical dental arch model by matching tooth models having the same unique registration marks.

The positive arch mold can also be digitized by a three-dimensional scanning using techniques such as laser scanning, optical scanning, destructive scanning, CT scanning and Sound Wave Scanning. A physical digital arch model is therefore obtained. The physical digital arch model is subsequently smoothed and segmented. Each segment can be physically fabricated by CNC based manufacturing to obtain individual tooth models. The physical digital arch model tracks and stores the positions of the individual tooth models. Unique registration marks can be added to the digital tooth models that can be made into a physical feature in CNC base manufacturing.

Examples of CNC based manufacturing include CNC based milling, Stereolithography, Laminated Object Manufacturing, Selective Laser Sintering, Fused Deposition Modeling, Solid Ground Curing, and 3D ink jet printing. Details of fabricating tooth models are disclosed in commonly assigned and above referenced US patent application titled "Method and apparatus for manufacturing and constructing a physical dental arch mode" by Huafeng Wen, filed Nov. 2, 2004, the content of which is incorporated herein by reference.

In another embodiment, the separated tooth models are assembled by geometry matching. The intact positive arch impression is first scanned to obtain a 3D physical digital arch model. Individual teeth are then scanned to obtain digital tooth models for individual teeth. The digital tooth models can be matched using rigid body transformations to match a physical digital arch model. due to complex shape of the arch, inter-proximal areas, root of the teeth and gingival areas may be ignored in the geometry match. High precision is required for matching features such as cusps, points, crevasses, the front faces and back faces of the teeth. Each tooth is sequentially matched to result in rigid body transformations corresponding to the tooth positions that can reconstruct an arch.

In another embodiment, the separated tooth models are assembled and registered with the assistance of a 3D point picking devices. The coordinates of the tooth models are picked up by 3D point picking devices such as stylus or Microscribe devices before separation. Unique registration marks can be added on each tooth model in an arch before separation. The tooth models and the registration marks can be labeled by unique IDs. The tooth arch can later be assembled by identifying tooth models having the same registration marks as were picked from the Jaw. 3D point picking devices can be used to pick the same points again for each tooth model to confirm the tooth coordinates.

In order to produce a base, positive dental arches are first produced together in 130. The positive dental arches can be made from a negative impression of the patient's arch by casting as described above. Separate positive arches are made for upper jaw and the lower jaw. A base can be separated into a plurality of components, each of which can be molded as described below. The whole base can be assembled together by the components after they are separately molded.

Figure 10:
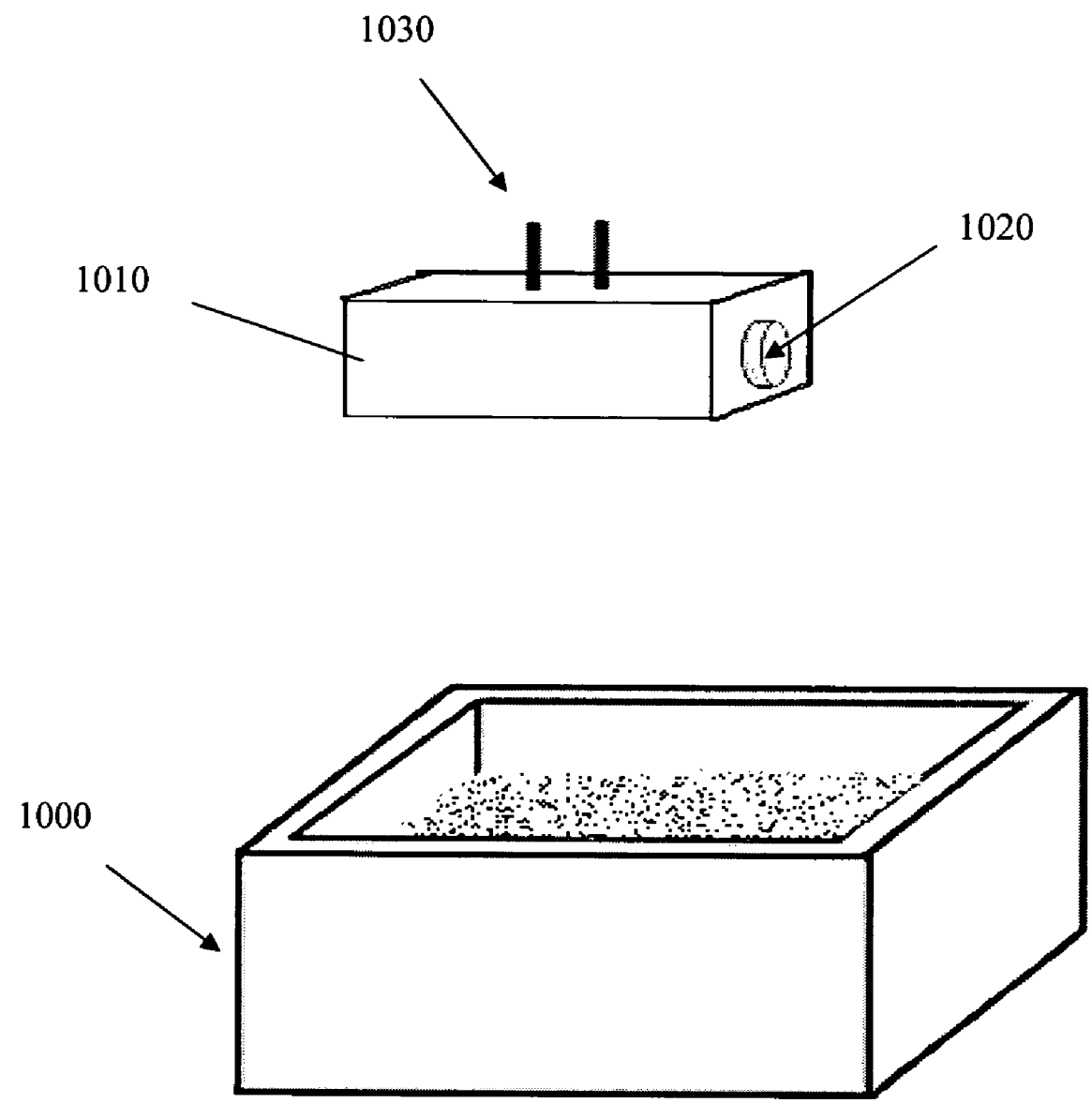
FIG. 10 illustrates a container for casting a dental base or base component that can receive physical tooth models.

A casting container 1000 is next prepared in step 140 for casting a base or a base component 1010 to support a physical dental arch model, as shown in FIG. 10. The base component 1010 can include features 1020 that allow a plurality of base components 1010 to be assembled to form a base. Features 1020 can for examples include sockets, holes, pins, and protrusions that allow the base components 1010 to tightly join or interlock to each other. The base component 1010 can include pins 1030 that can enable the mounting of one or more tooth models to the base component 1010.

A physical dental arch model can include a plurality of tooth models, which can represent a whole or portion of a patient's arch. A casting material such as epoxy, plaster or a mixture of materials is poured into the contained. The casting material can be a paste, a fluid, a thick mixture of polymeric, ceramic, or colloidal materials. Examples of casting materials include auto polymerizing acrylic resin, thermoplastic resin, light-polymerized acrylic resins, polymerizing silicone, polyether, plaster, epoxies, or a mixture of materials. The casting materials can include crosslinking agents to the cast materials to cause the polymerization and solidification of the cast materials having the impressions. The casting material can be irradiated by UV light through a window opened on the casting container ion to cause the polymerization and the solidification of the cast materials having the impressions.

The undersides of a positive dental arch are then pressed into the casting material. The casting material can then be solidified by heating or cooling. The casting material can also be irradiated by UV light through a window opened on the casting container ion to cause the polymerization and the solidification of the cast materials having the impressions. The container is opened and the mold can be removed. A base as shown in FIGS. 2,4,5,8 is obtained after the casting material is dried and solidified in step 150.

The solidification of the casting materials can be accomplished by non-uniform treatment by heating, cooling, UV or IR illuminations, or microwave radiation. For example, heating wires can laid out in the casting container to specifically heat the fine features in the impressions for receiving the physical tooth models. The casting material may also comprise non-uniform distribution of ingredients. For example, the concentration of the crosslinking agents may be higher near the fine features in the impressions for receiving the physical tooth models.

An advantage of the present invention is that a base or base component for receiving dental tooth models can be produced with simple, inexpensive and reliable methods and system. The casting chambers are can be used multiple times to reduce manufacturing cost.

Figure 11:
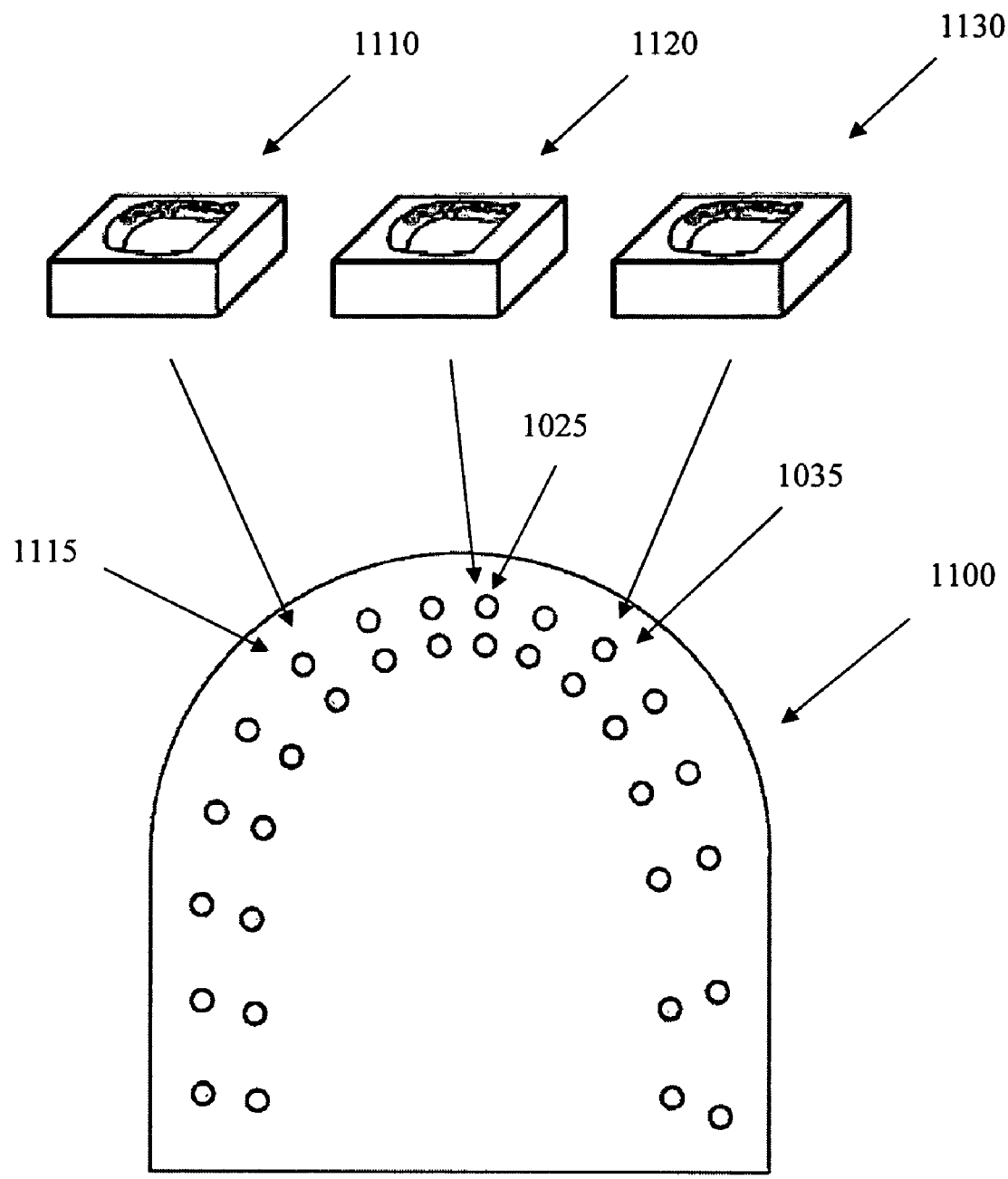
FIG. 11 illustrates a plurality of base components molded by a plurality of containers.

FIG. 11 illustrates a base 1100 comprising a plurality of base components 1115, 1125, 1135. The system of FIG. 11 does not cast the physical tooth, but the base of tooth or second feature which determines first feature locations and orientations. Each of the base components 1115, 1125, 1135 is configured to receive a physical tooth model and can molded by one of a plurality of casting containers 1110, 1120, 1130. The base components 1115, 1125, 1135 are assembled to form a dental base 1100 for receiving physical tooth models. The base components 1115, 1125, 1135 can include features to assist the assembly of the base components 1115, 1125, 1135 to form the base 1100 for the dental arch model. The features comprise one or more of a pin, a registration slot, a socket, a notch, a protrusion, a hole, an interlocking mechanism, a jig, and a pluggable or attachable feature. FIG. 11, 1110-1130 should have interconnect features, to allow one to connect to the other, or insert to a commen base to form an arch, these features should be small enough to avoid interference. The above features base be pre inserted to casting box, e.g, pins.

An advantage of the present invention is that the base component 1115, 1125, 1135 can be individually replaced for a different base configuration without changing the base components that are not changed in the orthodontic steps. The base can be molded in a plurality of base components 1115, 1125, 1135 that can be subsequently assembled to form the whole dental base. Only one base component 1010 of the base needs to be re-molded if the position of one physical tooth model is changed in an orthodontic treatment. This further reduces treatment costs.

Figure 12:
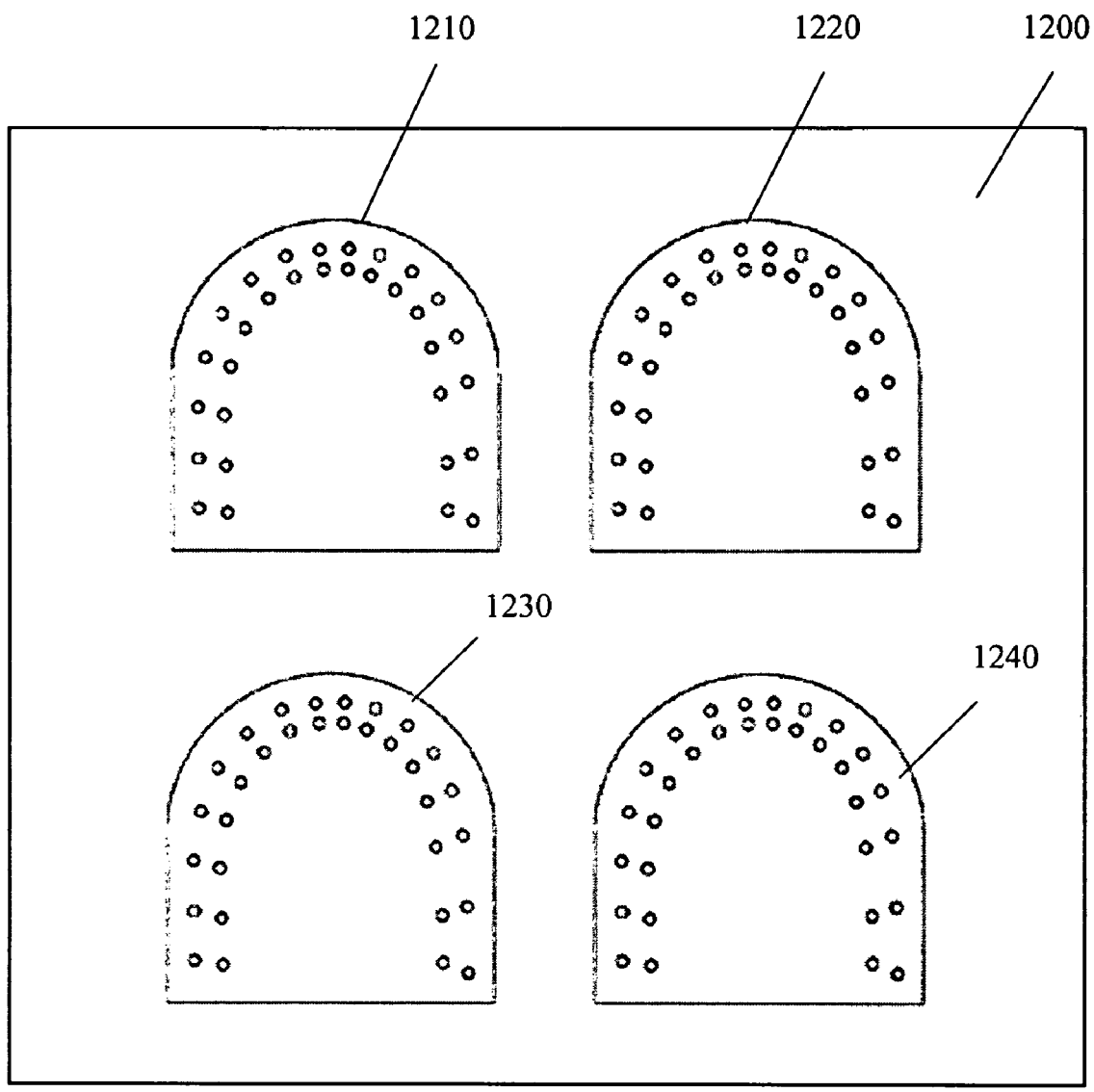
FIG. 12 a base comprising multiple sets of sockets for receiving a plurality of dental arches in different configurations.

FIG. 12 shows a base 1200 having multiple sets of sockets 1210, 1220, 1230, 1240, each of which can receive a dental arch in a different configuration. Different configurations of the base can be required during the process of an orthodontic treatment. The positions and orientations of the tooth models may differ step by step. The base can include a plurality of configurations in the sockets for the tooth models. Each configuration is adapted to receive the same physical tooth models to form a different arrangement of a tooth arch model.

In another embodiment, a positive impression is placed in a specially designed container as shown in FIG. 11. Casting material is then poured over the impression. A lid is subsequently placed top of the container for a specified period of time. The casting material can be solidified by heating or cooling. In another embodiment, UV light irradiated through a window opened on the casting container ion causes the polymerization and the solidification of the cast materials having the impressions. The container is opened and the mold can be removed. A base as shown in FIGS. 2,4,5,8 is obtained.

The base is made to receive the tooth models. The base and tooth models include complementary features to allow them to be assembled together. The tooth model has a protruding structure attached to it. The features at the base and tooth models can also include one or more of the following: a registration slot, a notch, a protrusion, a hole, an interlocking mechanism, and a jig. The protruding structure can be obtained during the casting process or be created after casting by using a CNC machine on each tooth. The positions of the receiving features in the base are determined by either the initial positions of the teeth in an arch or the desired teeth positions during a treatment process.

Figure 2:
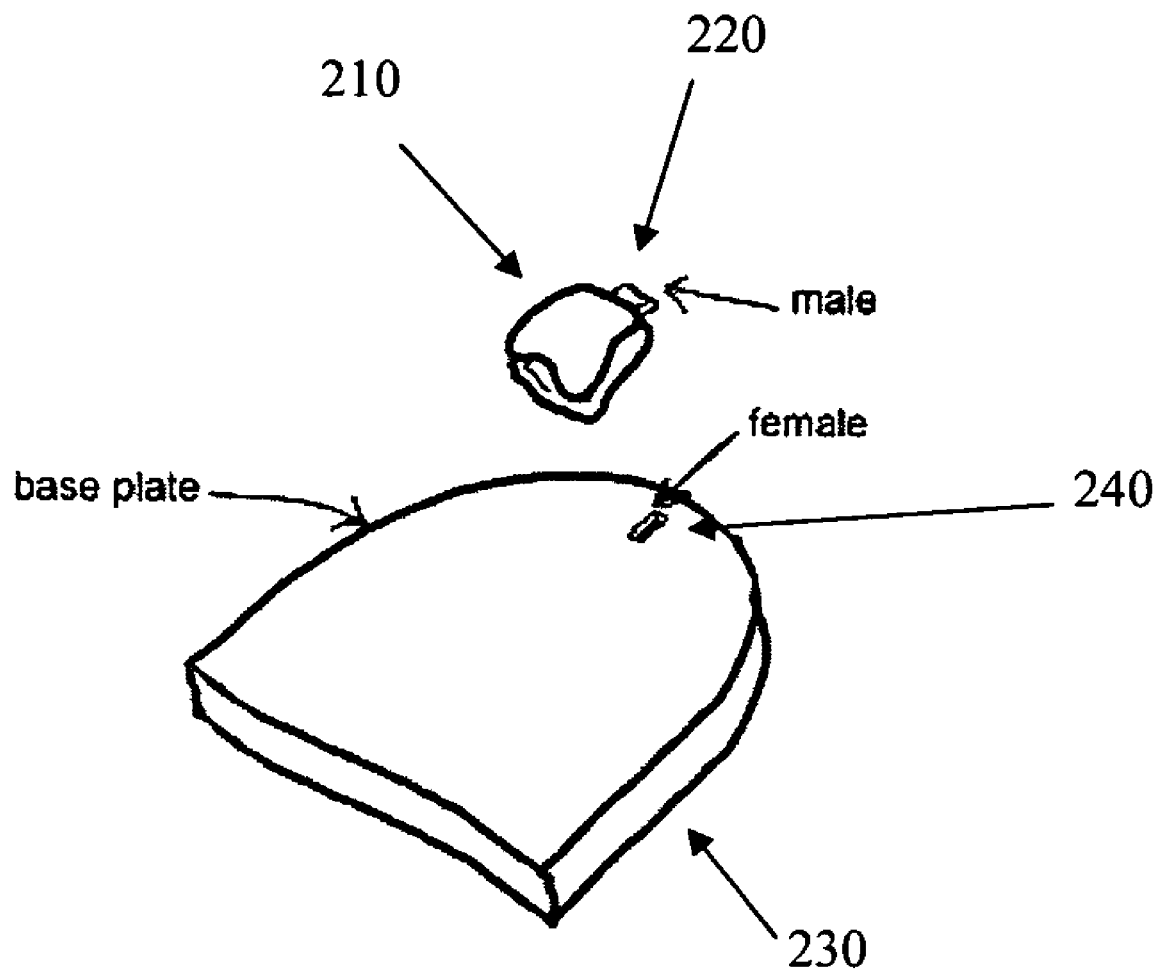
FIG. 2 illustrates a tooth model and a base respectively comprising complimentary features for assembling the tooth model with the base.

Before casting the arch from the impression, the base plate is taken through a CNC process to create the female structures for each individual tooth (step 150). Then the base is placed over the casting container in which the impression is already present and the container is filled with epoxy. The epoxy gets filled up in the female structures and the resulting mold has the male studs present with each tooth model that can be separated afterwards. FIG. 2 shows a tooth model 210 with male stud 220 after mold separation. The base 230 comprises a female feature 240 that can receive the male stud 220 when the tooth model 210 is assembled to the base 230.

Figure 3:
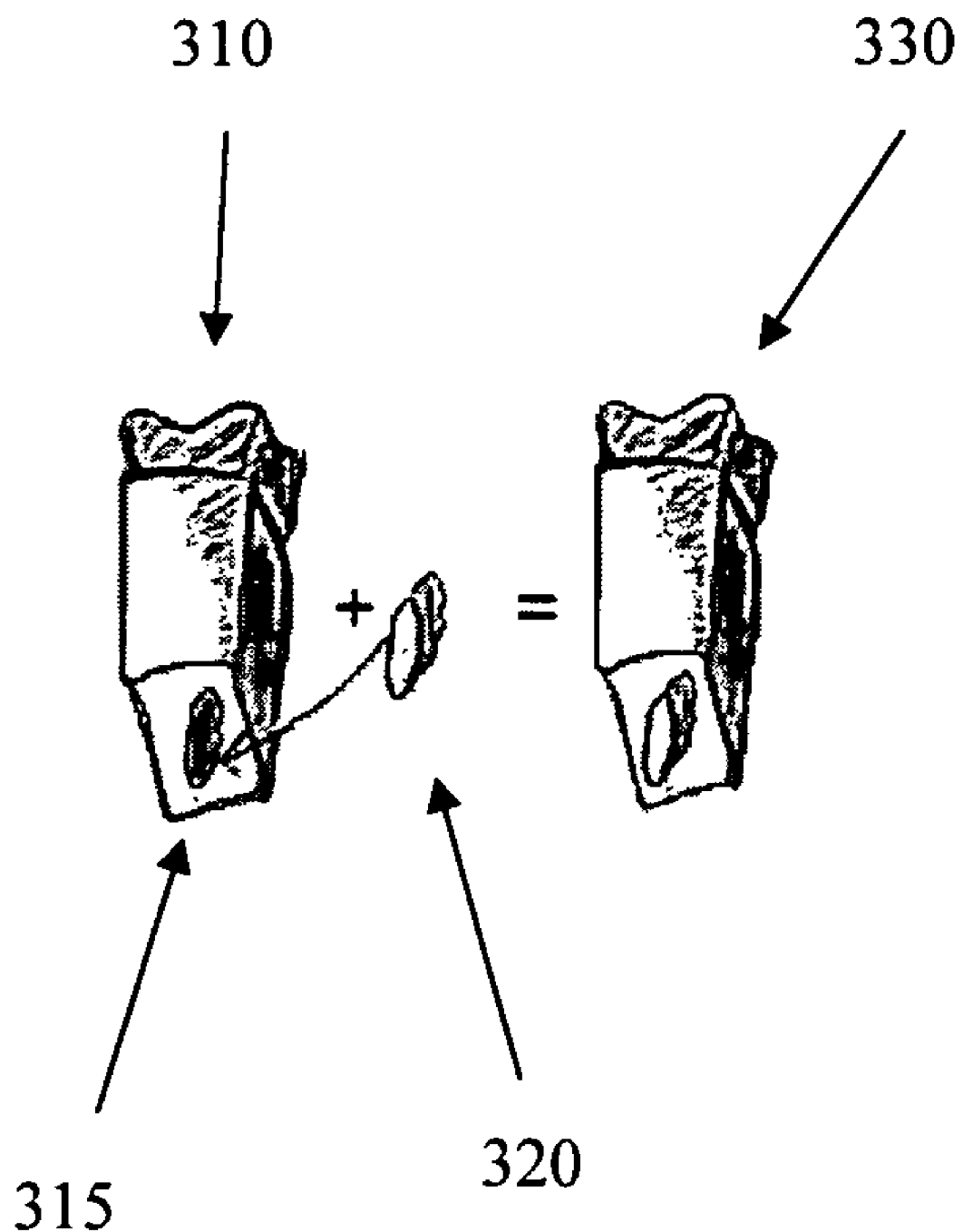
FIG. 3 illustrates fixing a stud to a tooth model with a female socket to produce a tooth model having a protruded stud.

Alternatively, as shown in FIG. 3, a tooth model 310 includes a female socket 315 that can be drilled by CNC based machining after casting and separation. A male stud 320 that fits the female socket 315 can be attached to the tooth model 310 by for example, screwing, glue application, etc. The resulted tooth model 330 includes male stud 310 that allows it to be attached to the base.

Figure 4:
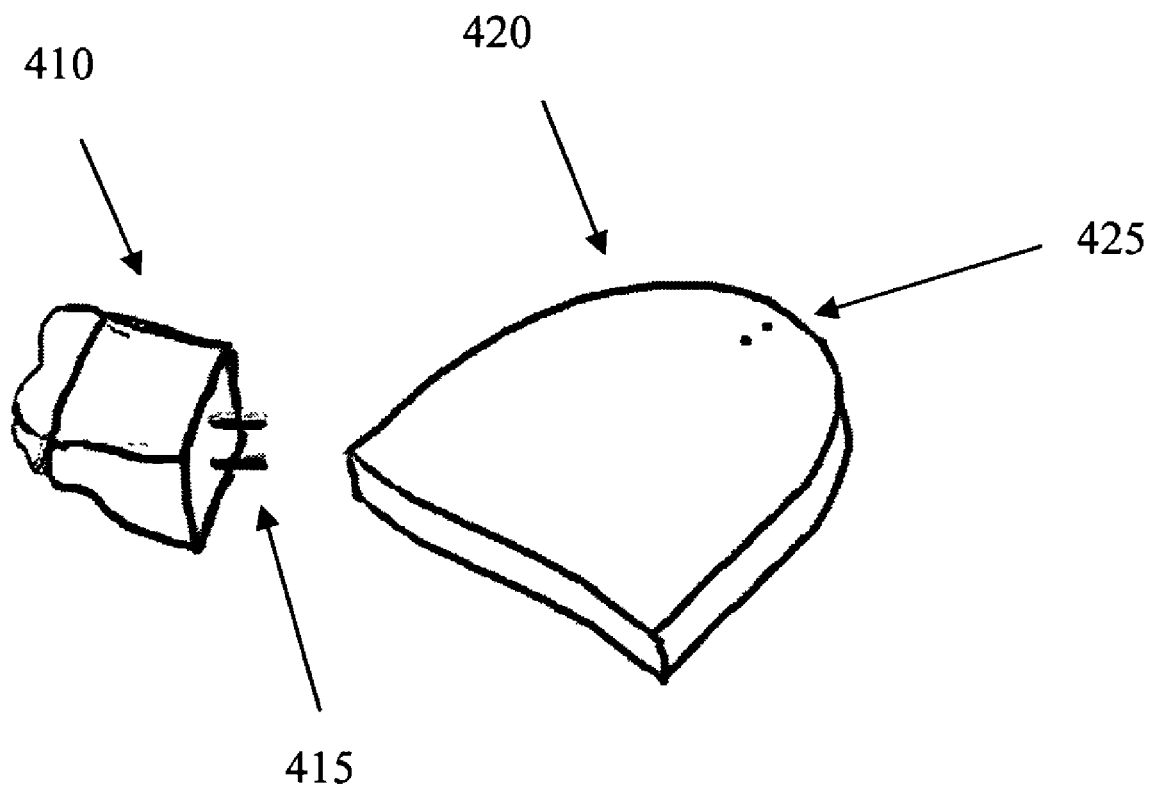
FIG. 4 illustrate a tooth model comprising two pins that allow the tooth model to be plugged into two corresponding holes in a base.
Figure 5:
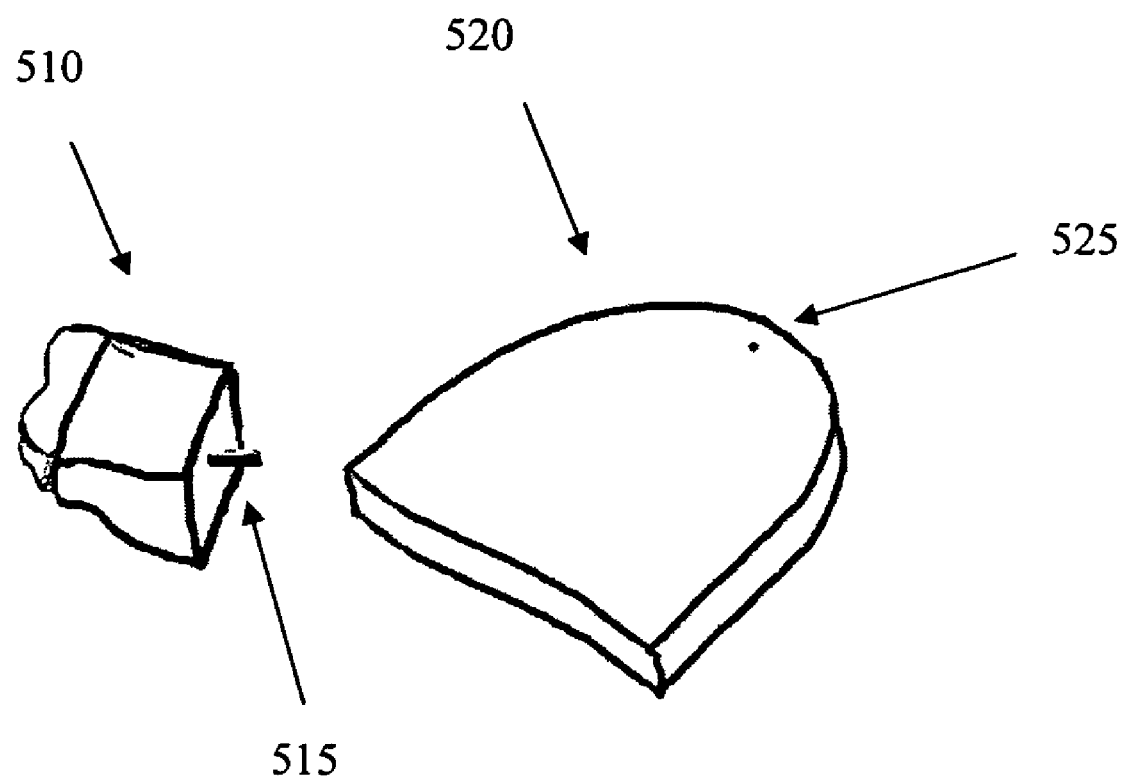
FIG. 5 illustrate a tooth model having a protruded pin that allows the tooth model to be plugged into a hole in a base.
Figure 6:
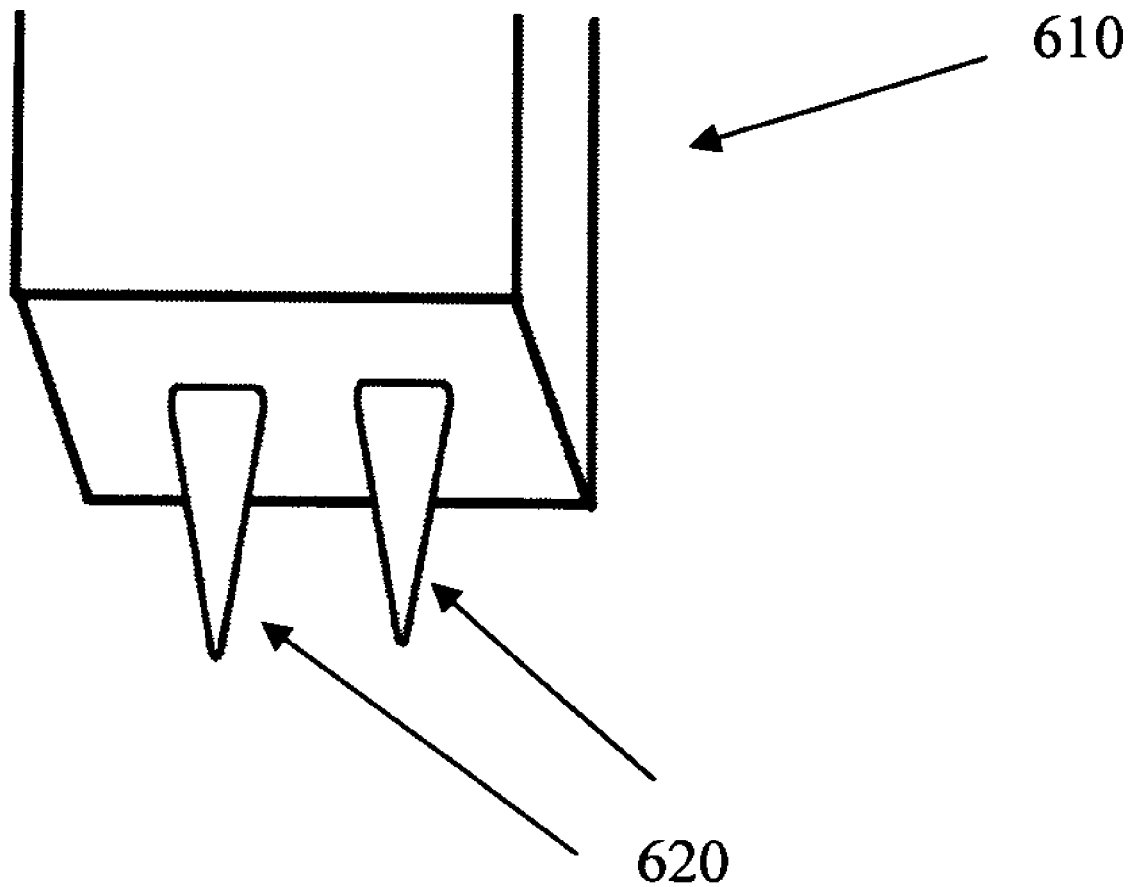
FIG. 6 illustrates cone shaped studs protruded out of the bottom of a tooth model.

Male protrusion features over the tooth model can be fabricated in a number of arrangements. FIG. 4 shows a tooth model 410 having two pins 415 protruding therefrom and a base 420 having registration slots 425 adapted to receive the two pins 415 to allow the tooth model 410 to be attached to the base 420. FIG. 5 shows a tooth model 510 having one pin 515 protruding out and a base 520 having a hole 525 adapted to receive the pin 515 to allow the tooth model 510 to be attached to the base 520. In general, the tooth model can include two or more pins wherein the base will have a corresponding number of holes at the corresponding locations for each tooth model. The tooth model 610 can also include cone shaped studs 620 as shown in FIG. 6. The studs can also take a combination of configurations described above.

Figure 7:
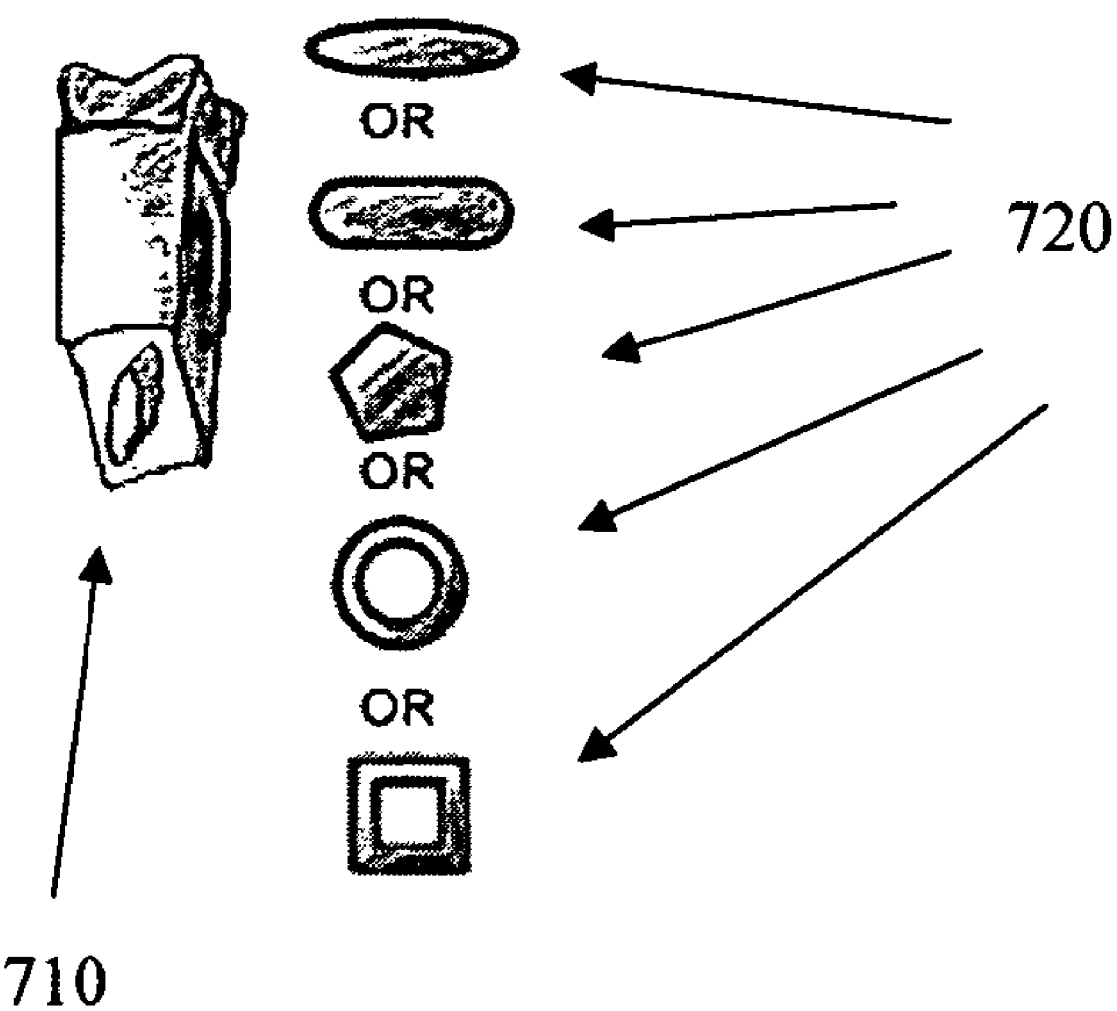
FIG. 7 illustrates exemplified shapes for the studs at the bottom of a tooth model.

As shown FIG. 7, the studs protruding from the tooth model 710 can take different shapes 720 such as oval, rectangle, square, triangle, circle, semi-circle, each of which correspond to slots on the base having identical shapes that can be drilled using the CNC based machining. The asymmetrically shaped studs can help to define a unique orientation for the tooth model on the base.

Figure 8A:
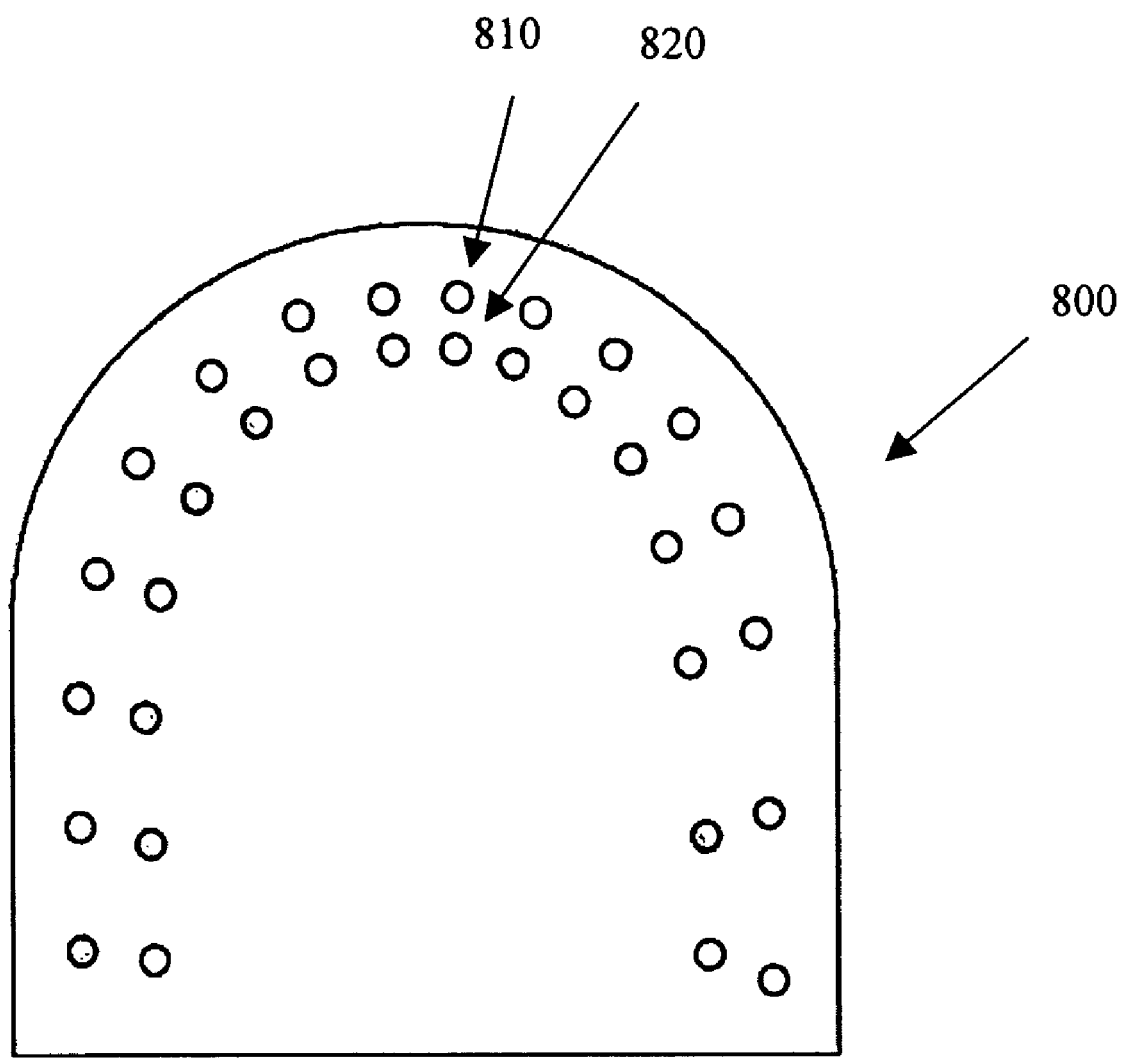
FIG. 8A illustrates an example of a base with a plurality of female sockets for receiving a plurality of tooth models for forming a physical dental arch model.

FIG. 8A shows a base 800 having a plurality of sockets 810 and 820 for receiving the studs of a plurality of tooth models. The positions of the sockets 810,820 are determined by either initial teeth positions in a patient's arch or the teeth positions during the orthodontic treatment process. The base 800 can be in the form of a plate as shown in FIG. 8, including a plurality of pairs of sockets 810,820. Each pair of sockets 810,820 is adapted to receive two pins associated with a physical tooth model. Each pair of sockets includes a socket 810 on the inside of the tooth arch model and a socket 820 on the outside of the tooth arch model.

Figure 8B:
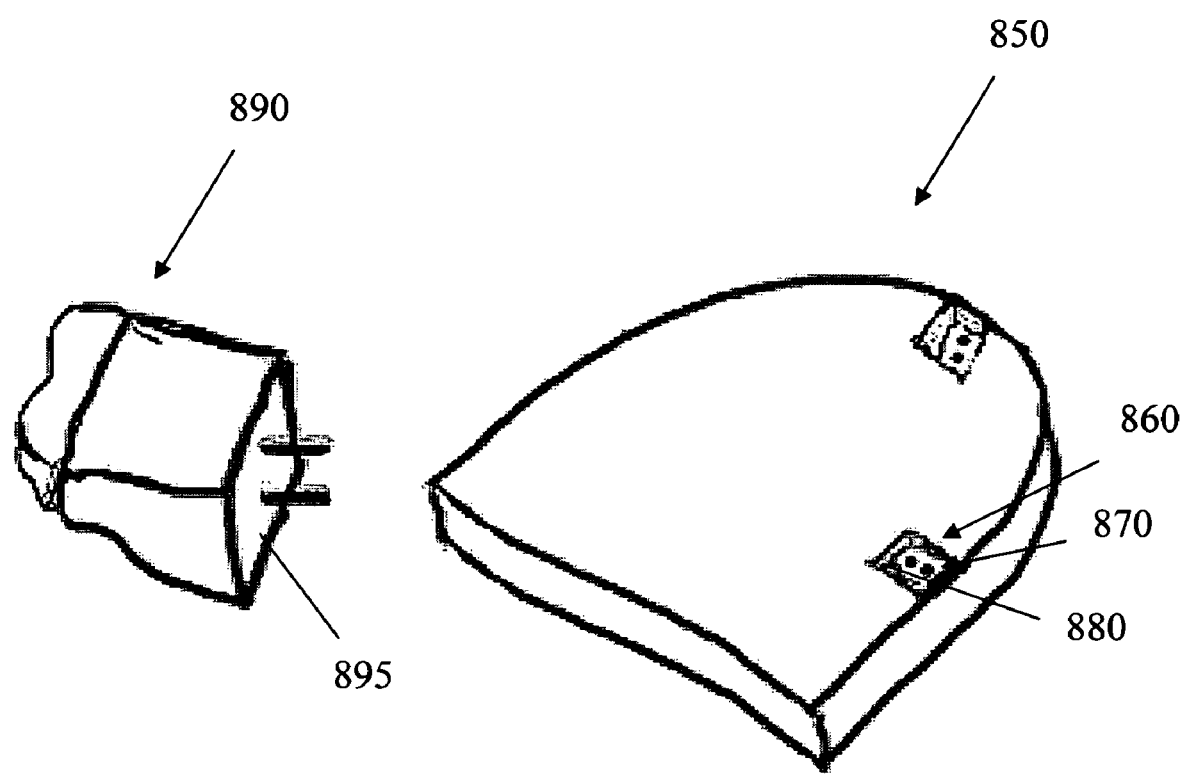
FIG. 8B illustrates another example of a base with a plurality of female sockets for receiving a plurality of tooth models for forming a physical dental arch model.

Another base 850 is shown in FIG. 8B. A plurality of pairs of female sockets 860, 870 are provided in the base 850. Each pair of the sockets 860, 870 is formed in a surface 880 and is adapted to receive a physical tooth model 890. The bottom portion of the physical tooth model 890 includes a surface 895. The surface 895 contacts the surface 880 when the physical tooth model 890 is inserted into the base 850, which assures the stability of the physical tooth model 890 over the base 850.

Figure 9:
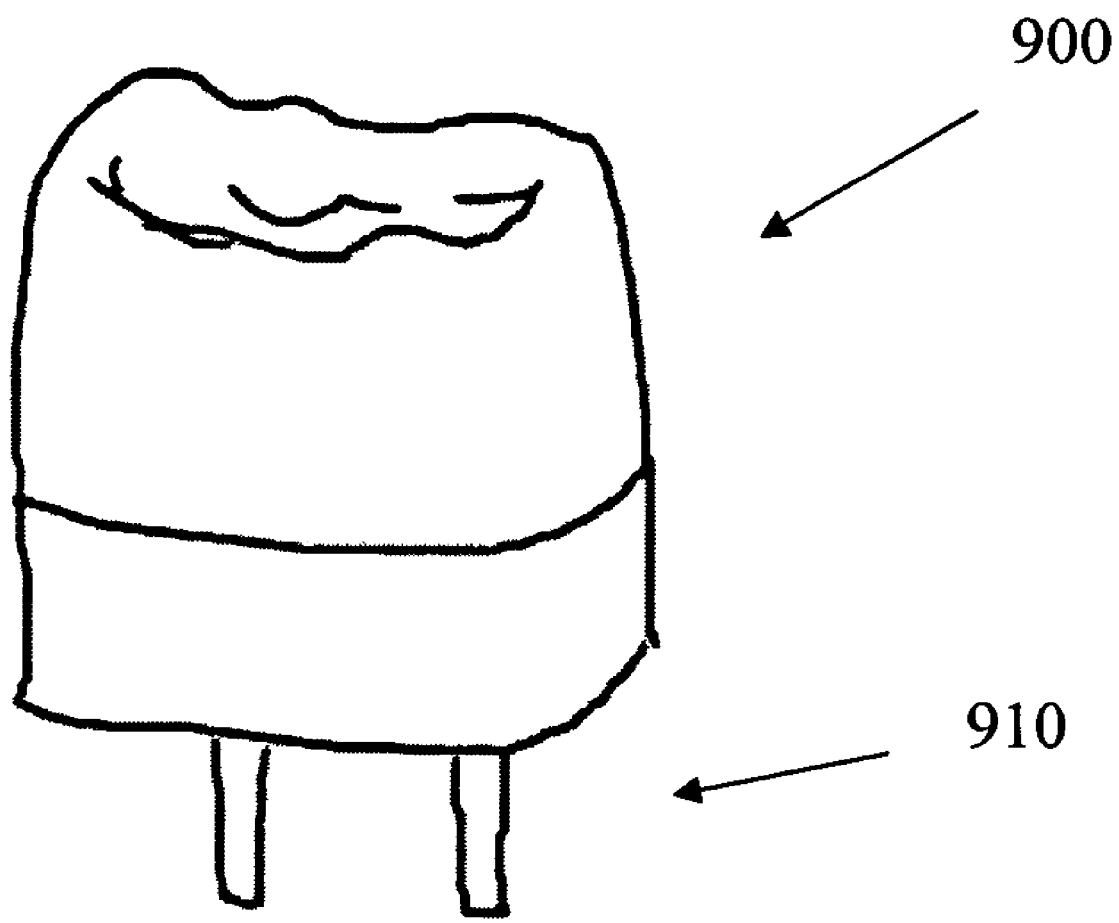
FIG. 9 illustrates a tooth model that can be assembled to the base in FIGS. 8A and 8B.

A tooth model 900 compatible with the base 800 is shown in FIG. 9. The tooth model 900 includes two pins 910 connected to its bottom portion. The two pins 910 can be plugged into a pair of sockets 810 and 820 on the base 800. Thus each pair of sockets 810 and 820 uniquely defines the positions of a tooth model. The orientation of the tooth model is also uniquely defined if the two pins are labeled as inside and outside, or the sockets and the pins are made asymmetric inside and outside. In general, each tooth model may include correspond to one or a plurality of studs that are to be plugged into the corresponding number of sockets. The male studs and the sockets may also take different shapes as described above.

A tooth arch model is obtained after the tooth models are assembled to the base 800 (step 160). The base 800 can have a plurality of configurations in the female sockets 810. Each of the configurations is adapted to receive the same physical tooth models to form a different arrangement of at least a portion of a tooth arch model. The different configurations can be required at different steps of orthodontic treatment.

The base 800 can be fabricated by a system that includes a computer device adapted to store digital tooth models representing the physical tooth models. As described above, the digital tooth model can be obtained by various scanning techniques. A computer processor can then generate a digital base model compatible with the digital tooth models. An apparatus fabricates the base using CNC based manufacturing in accordance with the digital base model. The fabricated base is adapted to receive the physical tooth models.

The physical tooth models can be identified or labeled by a predetermined sequence that define the positions of the physical tooth models on the base 800. The labels can include a barcode, a printed symbol, hand-written symbol, a Radio Frequency Identification (RFID). The female sockets 810 can also be labeled by the parallel sequence for the physical tooth models.

In one embodiment, tooth models can be separated from the base and repaired. The tooth models can be removed, repaired or replaced, and re-assembled without the replacement of the whole arch model.

Materials for the tooth models can include polymers, urethane, epoxy, plastics, plaster, stone, clay, acrylic, metals, wood, paper, ceramics, and porcelain. The base can comprise a material such as polymers, urethane, epoxy, plastics, plaster, stone, clay, acrylic, metals, wood, paper, ceramics, porcelain, glass, and concrete.

The arch model can be used in different dental applications such as dental crown, dental bridge, aligner fabrication, biometrics, and teeth whitening. For aligner fabrication, for example, each stage of the teeth treatment may correspond to a unique physical dental arch model. Removable appliances can be fabricated using different physical dental arch models one at a time as the teeth movement progresses during the treatment. At each stage of the treatment, the desirable teeth positions for the next stage are calculated. A physical dental arch model having modified teeth positions is fabricated using the process described above. A new aligner is made using the new physical dental arch model.

In accordance with one embodiment of the present invention, each base is specific to an arch configuration. There is no need for complex and costly mechanisms such as micro-actuators for adjusting multiple degrees of freedom for each tooth model. The described methods and system is simple to make and easy to use.

The described methods and system are also economical. Different stages of the arch model can share the same tooth models. The positions for the tooth models at each stage of the orthodontic treatment can be modeled using orthodontic treatment software. Each stage of the arch model may use a separate base. Or alternatively, one base can be used in a plurality of stages of the arch models. The base may include a plurality of sets of receptive positions for the tooth models. Each set corresponds to one treatment stage. The tooth models can be reused through the treatment process. Much of the cost of making multiple tooth arch models in orthodontic treatment is therefore eliminated.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method for producing a base to receive physical models of one or more teeth, comprising:
    providing a cast material in a container;
    impressing undersides of a plurality of individual physical tooth models into the cast material to produce impressions of the undersides in the cast material, said plurality of individual physical tooth models comprising a portion of a dental arch, wherein individual physical tooth models of said plurality of individual physical tooth models having been obtained in such a manner that said individual physical tooth models may be joined with each other to form said portion of said dental arch;
    solidifying the cast material with the impressions to produce a base configured to receive the plurality of individual physical tooth models; and
    labeling the plurality of individual physical tooth models in a predetermined sequence.

2. The method of claim 1, wherein the cast material consists of one or more of a polymer, a thermal elastic material, a urethane, an epoxy, a plaster, a clay, an acrylic, a latex, a dental PVS, a resin, a metal, an aluminum material, an ice material, and a wax material.

3. The method of claim 1 further comprising:
    defining the positions of the impressions on the base in accordance with a patient's arch.

4. The method of claim 1, comprising heating or cooling the cast materials to cause the solidification of the cast materials having the impressions.

5. The method of claim 1, wherein solidifying the cast material comprises applying at least one of microwave radiation, ultraviolet radiation and infrared radiation.

6. The method of claim 1, further comprising applying one or more crosslinking agents to the cast materials to cause polymerization and solidification of the cast materials having the impressions.

7. The method of claim 1, wherein the plurality of individual physical tooth models comprise first features to assist the reception of the plurality of individual physical tooth models by the base.

8. The method of claim 7, wherein the features consists of one or more of a pin, a registration slot, a notch, a protrusion, a hole, an interlocking mechanism, a jig, and a pluggable or attachable feature.

9. The method of claim 7, wherein the impressions in the base comprise second features complementary to the first features to assist the reception of the plurality of individual physical tooth models by the base.

10. The method of claim 1, further comprising:
    placing the plurality of individual physical tooth models in a container;
    wherein impressing the undersides of the plurality of individual physical tooth models into the cast material comprises pouring the cast material over the underside of the plurality of individual physical tooth models in the container.

11. The method of claim 1, further comprising assembling the base with one or more additional bases to form a dental arch model.

12. The method of claim 1, wherein the predetermined sequence defines the positions of the plurality of individual physical tooth models on the base.

13. A method for producing a base to receive physical models of one or more teeth, comprising:
    providing a cast material in a container;
    impressing undersides of a plurality of individual physical tooth models into the cast material to produce impressions of the undersides in the cast material, said plurality of individual physical tooth models comprising a portion of a dental arch, wherein individual physical tooth models of said plurality of individual physical tooth models having been obtained in such a manner that said individual physical tooth models may be joined with each other to form said portion of said dental arch; and
    solidifying the cast material with the impressions to produce a base configured to receive the plurality of individual physical tooth models, said solidifying comprising applying radiation.

14. The method of claim 13, wherein the cast material consists of one or more of a polymer, a thermal elastic material, a urethane, an epoxy, a plaster, a clay, an acrylic, a latex, a dental PVS, a resin, a metal, an aluminum material, an ice material, and a wax material.

15. The method of claim 13, comprising:
    labeling the plurality of individual physical tooth models in a predetermined sequence that defines the positions of the plurality of individual physical tooth models on the base.

16. The method of claim 13 further comprising:
    defining the positions of the impressions on the base in accordance with a patient's arch.

17. The method of claim 13, wherein the plurality of individual physical tooth models comprise first features to assist the reception of the plurality of individual physical tooth models by the base.

18. The method of claim 17, wherein the features consists of one or more of a pin, a registration slot, a notch, a protrusion, a hole, an interlocking mechanism, a jig, and a pluggable or attachable feature.

19. The method of claim 17, wherein the impressions in the base comprise second features complementary to the first features to assist the reception of the plurality of individual physical tooth models by the base.

20. The method of claim 13, further comprising:
placing the plurality of individual physical tooth models in a container;
wherein impressing the undersides of the plurality of individual physical tooth models into the cast material comprises pouring the cast material over the underside of the plurality of individual physical tooth models in the container.

21. The method of claim 13, further comprising assembling the base with one or more additional bases to form a dental arch model.

22. The method of claim 13, wherein the radiation comprises microwave radiation.

23. The method of claim 13, wherein the radiation comprises ultraviolet radiation.

24. The method of claim 13, wherein the radiation comprises infrared radiation.

25. A method for producing a base to receive physical models of one or more teeth, comprising:
providing a cast material in a container;
impressing undersides of a plurality of individual physical tooth models into the cast material to produce impressions of the undersides in the cast material, said plurality of individual physical tooth models comprising a portion of a dental arch, wherein individual physical tooth models of said plurality of individual physical tooth models having been obtained in such a manner that said individual physical tooth models may be joined with each other to form said portion of said dental arch; and
solidifying the cast material with the impressions to produce a base configured to receive the plurality of individual physical tooth models, said solidifying comprising applying one or more crosslinking agents to the cast material to cause polymerization.

26. The method of claim 25, wherein the cast material consists of one or more of a polymer, a thermal elastic material, a urethane, an epoxy, a plaster, a clay, an acrylic, a latex, a dental PVS, a resin, a metal, an aluminum material, an ice material, and a wax material.

27. The method of claim 25 further comprising:
defining the positions of the impressions on the base in accordance with a patient's arch.

28. The method of claim 25, wherein the plurality of individual physical tooth models comprise first features to assist the reception of the plurality of individual physical tooth models by the base.

29. The method of claim 28, wherein the features consists of one or more of a pin, a registration slot, a notch, a protrusion, a hole, an interlocking mechanism, a jig, and a pluggable or attachable feature.

30. The method of claim 28, wherein the impressions in the base comprise second features complementary to the first features to assist the reception of the plurality of individual physical tooth models by the base.

31. The method of claim 25, further comprising:
placing the plurality of individual physical tooth models in a container;
wherein impressing the undersides of the plurality of individual physical tooth models into the cast material comprises pouring the cast material over the underside of the plurality of individual physical tooth models in the container.

32. The method of claim 25, further comprising assembling the base with one or more additional bases to form a dental arch model.

* * * * *